US010898712B2

(12) United States Patent
Frühauf et al.

(10) Patent No.: US 10,898,712 B2
(45) Date of Patent: Jan. 26, 2021

(54) ROBUST INSTANTANEOUS FREQUENCY ESTIMATION FOR HEARING PROSTHESIS SOUND CODING

(71) Applicant: MED-EL Elektromedizinische Geraete GmbH, Innsbruck (AT)

(72) Inventors: Florian Frühauf, Rinn (AT); Peter Schleich, Telfs (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 164 days.

(21) Appl. No.: 15/770,287

(22) PCT Filed: Oct. 19, 2016

(86) PCT No.: PCT/US2016/057585
§ 371 (c)(1),
(2) Date: Apr. 23, 2018

(87) PCT Pub. No.: WO2017/070138
PCT Pub. Date: Apr. 27, 2017

(65) Prior Publication Data
US 2018/0311500 A1 Nov. 1, 2018

Related U.S. Application Data

(60) Provisional application No. 62/245,361, filed on Oct. 23, 2015.

(51) Int. Cl.
*A61N 1/36* (2006.01)
*A61N 1/05* (2006.01)
*H04R 25/00* (2006.01)

(52) U.S. Cl.
CPC ....... *A61N 1/36038* (2017.08); *A61N 1/0541* (2013.01); *H04R 25/505* (2013.01)

(58) Field of Classification Search
CPC . A61N 1/36038; A61N 1/0541; H04R 25/505
See application file for complete search history.

(56) References Cited

U.S. PATENT DOCUMENTS

| 5,214,708 A | 5/1993 | McEachern |
| 8,417,348 B2 | 4/2013 | Schleich |

(Continued)

FOREIGN PATENT DOCUMENTS

| CN | 101055717 A | 10/2007 |
| CN | 101854978 A | 10/2010 |

(Continued)

OTHER PUBLICATIONS

International Searching Authority, International Search Report—International Application No. PCT/US2016/057585, dated Dec. 23, 2016, together with the Written Opinion of the International Searching Authority, 15 pages.

(Continued)

*Primary Examiner* — Rex R Holmes
(74) *Attorney, Agent, or Firm* — Sunstein LLP

(57) ABSTRACT

A signal processing arrangement generates electrical stimulation signals to electrode contacts in an implanted cochlear implant array. An input sound signal is processed to generate band pass signals that each represent an associated band of audio frequencies. A characteristic envelope signal is extracted for each band pass signal based on its amplitude. Stimulation timing signals are generated for each band pass signal, including for one or more selected band pass signals using a timing function defined to: i. represent instantaneous frequency as determined by the band pass signal temporal fine structure features, and ii. exclude temporal fine structure features occurring within a time period shorter than a band-specific upper frequency limit. The electrode stimula- (Continued)

tion signals are produced for each electrode contact based on the envelope signals and the stimulation timing signals.

21 Claims, 16 Drawing Sheets

(56) References Cited

U.S. PATENT DOCUMENTS

| | | | |
|---|---|---|---|
| 8,577,473 | B2 | 11/2013 | Schleich et al. |
| 2009/0287492 | A1 | 11/2009 | Chalupper et al. |
| 2012/0004706 | A1* | 1/2012 | Meister ............... A61N 1/36038 607/57 |
| 2012/0209351 | A1* | 8/2012 | Meister ............... A61N 1/36036 607/57 |
| 2012/0303093 | A1 | 11/2012 | Wouters et al. |
| 2014/0107730 | A1 | 4/2014 | Zierhofer |
| 2015/0080980 | A1 | 3/2015 | Meister et al. |
| 2015/0163604 | A1* | 6/2015 | Fruhauf ............... A61N 1/3606 607/57 |
| 2015/0163605 | A1* | 6/2015 | Meister ............... A61N 1/36032 607/57 |

FOREIGN PATENT DOCUMENTS

| | | |
|---|---|---|
| CN | 102958561 A | 3/2013 |
| CN | 103140260 A | 6/2013 |
| CN | 104107505 A | 10/2014 |
| CN | 104856784 A | 8/2015 |
| WO | WO 2015/026690 A1 | 2/2015 |
| WO | WO 2015/042091 A1 | 3/2015 |
| WO | WO 2015/054090 A1 | 4/2015 |

OTHER PUBLICATIONS

European Patent Office, Extended European Search Report, Application No. 16858084.3, dated Oct. 8, 2018, 6 pages.

China National Intellectual Property Administration, First Office Action, Application No. 201680061918.4, dated Oct. 22, 2019, 6 pages.

China National Intellectual Property Administration, Notification of the Second Office Action, Application No. 201680061918.4, dated Jul. 6, 2020, with English translation, 6 pages.

\* cited by examiner

ROBUST INSTANTANEOUS FREQUENCY ESTIMATION FOR HEARING PROSTHESIS SOUND CODING

This application is a 371 national phase entry of Patent Cooperation Treaty Application PCT/US16/57585, filed Oct. 19, 2016, which in turn claims priority from U.S. Provisional Patent Application 62/245,361, filed Oct. 23, 2015, which is incorporated herein by reference in its entirety.

FIELD OF THE INVENTION

The present invention relates to hearing implant systems, and more specifically, to techniques for producing electrical stimulation signals in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties).

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 μs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference. The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

Many cochlear implant coding strategies use what is referred to as an n-of-m approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc.

Fine structure coding strategies such as FSP and FS4 use the zero-crossings of the band-pass signals to start a channel-specific sampling sequence (CSSS) pulse sequences for delivery to the corresponding electrode contact. Zero-crossings reflect the dominant instantaneous frequency quite robustly in the absence of other spectral components. But in the presence of higher harmonics and noise, problems can arise. See, e.g., WO 2010/085477 and Gerhard, David, Pitch *extraction and fundamental frequency: History and current techniques*, Regina: Department of Computer Science, University of Regina, 2003; both incorporated herein by reference in their entireties.

FIG. 2 shows an example of a spectrogram for a sample of clean speech including estimated instantaneous frequencies for Channels 1 and 3 as reflected by evaluating the signal zero-crossings, indicated by the vertical dashed lines. The horizontal black dashed lines show the channel frequency boundaries—Channels 1, 2, 3 and 4 range between 100, 198, 325, 491 and 710 Hz, respectively. It can be seen in FIG. 2 that during periods of a single dominant harmonic in a given frequency channel, the estimate of the instantaneous frequency is smooth and robust; for example, in Channel 1 from 1.6 to 1.9 seconds, or in Channel 3 from 3.4 to 3.5 seconds. When additional frequency harmonics are present in a given channel, or when the channel signal intensity is low, the instantaneous frequency estimation becomes inaccurate, and, in particular, the estimated instantaneous frequency may even leave the frequency range of the channel.

Gerhard 2003 cited above gives an overview of algorithms that can be used to estimate the fundamental frequency. These algorithms include time-domain methods, frequency-domain methods and statistical frequency-domain methods. Most of them are computationally too expensive to be usable in real life and/or cannot guarantee robustness. Vandali et al. "Pitch ranking ability of cochlear implant recipients: A comparison of sound-processing strategies." *The Journal of the Acoustical Society of America* 117.5 (2005): 3126-3138 (incorporated herein by reference in its entirety) uses positive peaks instead of the zero-crossings to preserve the fine structure information. But peak detection has the same problems as the zero-crossings technique when more than one harmonic and/or noise occurs in a given frequency channel.

In WO 2010/085477, the filter bank resolution is enhanced to resolve the low frequency harmonics. As a result, the estimation of the instantaneous frequency is robust when using the zero-crossing approach. A signal-dependent algorithm also is used to select channels of the high-resolution bands, which are then sent to the implant.

SUMMARY OF THE INVENTION

Embodiments of the present invention are directed to a signal processing arrangement and corresponding method that generates electrode stimulation signals to electrode contacts in an implanted cochlear implant array. An input sound signal is processed to generate band pass signals that each represent an associated band of audio frequencies. A characteristic envelope signal is extracted for each band pass signal based on its amplitude. Stimulation timing signals are generated for each band pass signal, including, for one or more selected band pass signals, using a timing function defined to: i. represent instantaneous frequency as determined by the band pass signal temporal fine structure features, and ii. exclude temporal fine structure features occurring within a time period shorter than a band-specific upper frequency limit. The electrode stimulation signals are produced for each electrode contact based on the envelope signals and the stimulation timing signals.

In further specific embodiments, the band pass signal temporal fine structure features used by the timing function may specifically include zero crossings of the band pass signal. The stimulation timing signals for the one or more selected band pass signals specifically may be Channel-Specific Sampling Sequences (CSSS). The timing function may further be defined either to preserve fine structure interaural time difference (ITD) information present in the input sound signal, or without regard to preserving fine structure interaural time difference (ITD) information present in the input sound signal. Extracting the characteristic envelope signals may include using low pass filters or Hilbert filters. The stimulation timing signals for some band pass signals may be generated without the timing function, using Continuous Interleaved Sampling (CIS) coding.

In some embodiments, the timing function may further be defined to exclude temporal fine features occurring outside a timing smoothing window defined by updated fine structure feature history. The timing smoothing window may be defined using a voice activity detector (VAD). And the timing function may further be defined to identify an onset period of the band pass envelope signal and application the timing smoothing window during the onset period.

BRIEF DESCRIPTION OF THE DRAWINGS

The file of this patent contains at least one photograph. Copies of this patent with photograph will be provided by the Office upon request and payment of the necessary fee.

DETAILED DESCRIPTION OF SPECIFIC EMBODIMENTS

The bandwidths of the band pass filters in a typical cochlear implant signal processor are quite large compared to the auditory filters in normal hearing, and there is likely to be more than one frequency harmonic in each electrode channel. This can cause a poor estimation of the instantaneous frequency of the dominant harmonic in a given channel. Embodiments of the present invention are based on a modified starting point of the stimulation timing events in which the instantaneous frequency is estimated more robustly than with the existing zero-crossing technique even if more than one harmonic and/or noise is present in the channel. This may improve speech intelligibility and perception of music and pitch without requiring special high resolution filter banks. And some embodiments can preserve the fine structure ITD information present in the low frequencies. In addition, the processing algorithms have low complexity and can be easily incorporated into existing cochlear implant signal processors.

Figure 3:
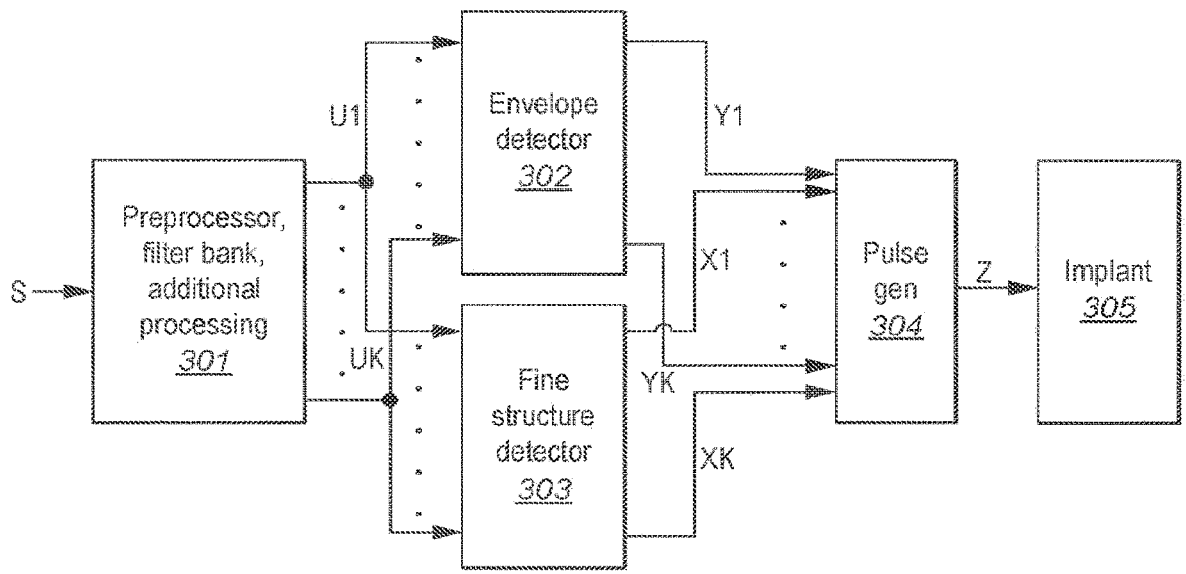
FIG. 3 shows various functional blocks in a signal processing arrangement for a hearing implant according to an embodiment of the present invention.
Figure 4:
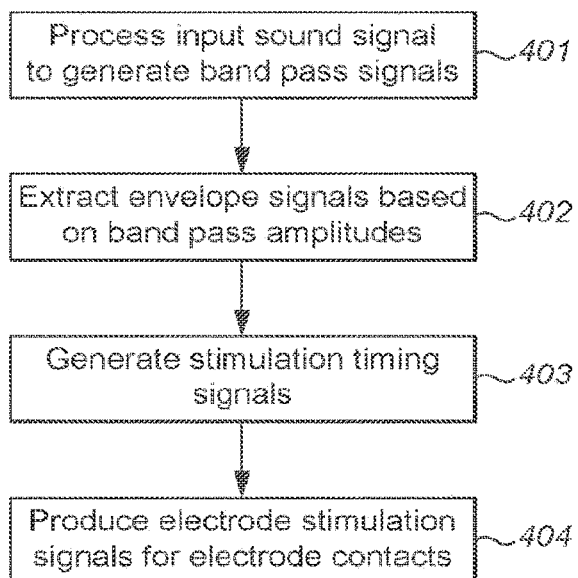
FIG. 4 shows various logical steps in developing electrode stimulation signals according to an embodiment of the present invention.

FIG. 3 shows various functional blocks in a signal processing arrangement for a hearing implant and FIG. 4 is a flow chart showing various logical steps in producing electrode stimulation signals to electrode contacts in an implanted cochlear implant array according to an embodiment of the present invention. A pseudo code example of such a method can be set forth as:

Input Signal Preprocessing:

BandPassFilter (input_sound, band_pass_signals)
Envelope Extraction:

BandPassEnvelope (band_pass_signals, band_pass_envelopes)
Stimulation Timing Generation:

TimingGenerate (band_pass_signals, stim_timing)
Pulse Generation:

PulseGenerate (band_pass_envelopes, stim_timing, out_pulses)

The details of such an arrangement are set forth in the following discussion.

In the arrangement shown in FIG. 3, the initial input sound signal is produced by one or more sensing microphones, which may be omnidirectional and/or directional. Preprocessor Filter Bank 301 pre-processes this input sound signal, step 401, with a bank of multiple parallel band pass filters (e.g. Infinite Impulse Response (IIR) or Finite Impulse Response (FIR)), each of which is associated with a specific band of audio frequencies; for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 301. The Preprocessor Filter Bank 301 also may perform other initial signal processing functions such as and without limitation automatic gain control (AGC) and/or noise reduction and/or wind noise reduction and/or beamforming and other well-known signal enhancement functions.

Figure 5:
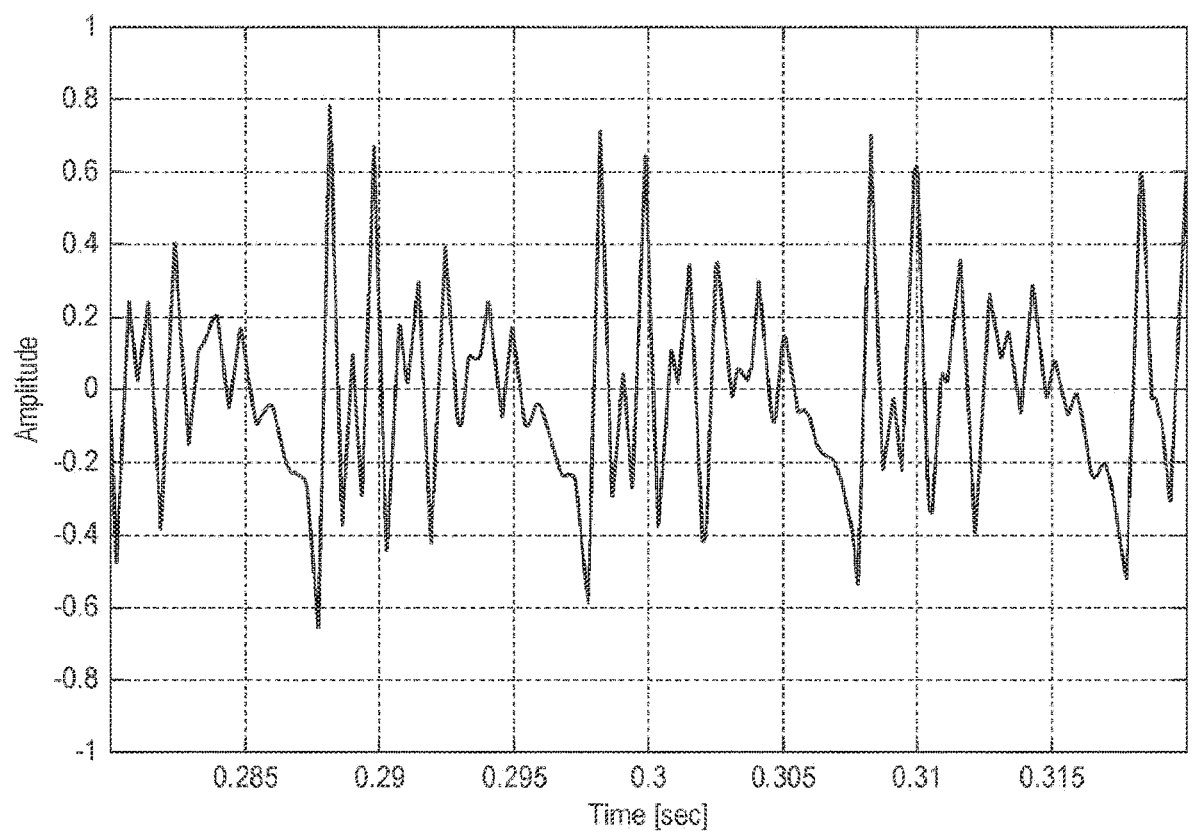
FIG. 5 shows an example of a short time period of an audio speech signal from a microphone.
Figure 6:
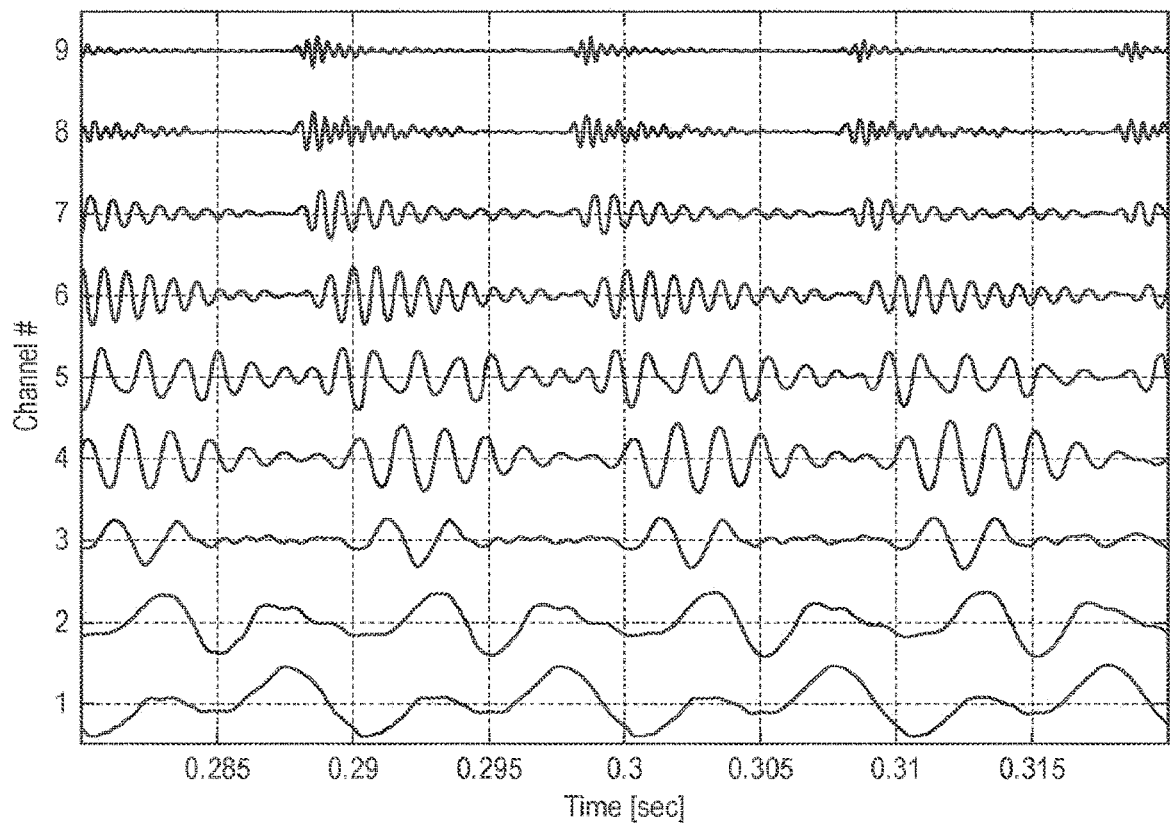
FIG. 6 shows an acoustic microphone signal decomposed by band-pass filtering by a bank of filters into a set of band pass signals.

FIG. 5 shows an example of a short time period of an input speech signal from a sensing microphone, and FIG. 6 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $U_1$ to $U_K$ (which can also be thought of as electrode channels) are output to an Envelope Detector 302 and Fine Structure Detector 303. The Envelope Detector 302 extracts characteristic envelope signals outputs $Y_1, \ldots, Y_K$, step 402, that represent the channel-specific band pass envelopes. The envelope extraction can be represented by $Y_k=LP(|U_k|)$, where $|\cdot|$ denotes the absolute value and $LP(\cdot)$ is a low-pass filter; for example, using 12 rectifiers and 12 digital Butterworth low pass filters of 2nd order, IIR-type. Alternatively, the Envelope Detector 302 may extract the Hilbert envelope, if the band pass signals $U_1, \ldots, U_K$ are generated by orthogonal filters.

The Fine Structure Detector 303 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$, step 403. In the following discussion, the band pass signals $U_1, \ldots, U_k$ are assumed to be real valued signals, so in the specific case of an analytic orthogonal filter bank, the Fine Structure Detector 303 considers only the real valued part of $U_k$. The Fine Structure Detector 303 is formed of K independent, equally-structured parallel sub-modules.

Figure 7:
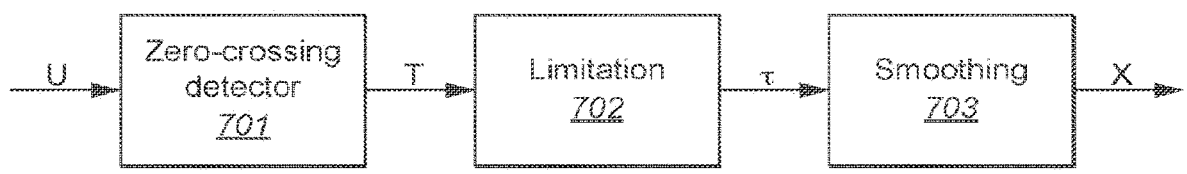
FIG. 7 shows various functional blocks in a fine structure detector according to an embodiment of the present invention.

FIG. 7 shows various functional blocks in one of these K sub-modules. The Zero-Crossing Detector 701 receives an input of the real valued signal $U_k$ of one band pass channel, and its output $T_k$ is generated when a given temporal fine structure feature occurs; e.g., a positive-to-negative zero-crossing of $U_k$. To simplify the further discussion, the channel index k is ignored. T[n] denotes the time when the $n^{th}$ zero-crossing of U is detected. The instantaneous frequency of U then can be estimated by $$f_{zc}[n] = \frac{1}{T[n] - T[n-1]}.$$

Referring back to FIG. 2, it shows a spectrogram of a clean speech signal and the estimated instantaneous frequencies $f_{zc}$ of Channels 1 and 3 generated by the Zero Crossing Detector 701. It can be seen in FIG. 2 that during periods of one dominant harmonic in a channel, $f_{zc}$ is smooth and robust; for example, in Channel 1 from 1.6 to 1.9 seconds, and in Channel 3 from 3.4 to 3.5 seconds. But when more than one harmonic is present in a channel, or during low-energy signal periods, the estimation of instantaneous frequency by the Zero Crossing Detector 701 alone will be irregular and insufficient. In particular, $f_{zc}$ might even be estimated beyond the frequency range of the channel. To avoid such errors, the Fine Structure Detector 303 follows the Zero Crossing Detector 701 with a Limitation Module 702 and a Smoothing Module 703 arranged to exclude unreliable temporal fine structure features.

In the Limitation Module 702, the range of the estimated frequency is limited to a band-specific upper frequency limit $f_{up}$. This involves ignoring zero-crossings that occur within a too short time period after the preceding zero-crossing. So the output of the Limitation Module 702, i.e. the point in time where the limited zero-crossing is detected, is set to $$\tau[m] = T[n] \text{ if } T[n] \geq \tau[m-1] + \frac{1}{f_{up}}.$$

Otherwise, the zero-crossing T[n] is ignored. The estimated instantaneous frequency is then denoted by $$f_\tau[m] = \frac{1}{\tau[m] - \tau[m-1]}.$$

Figure 8:
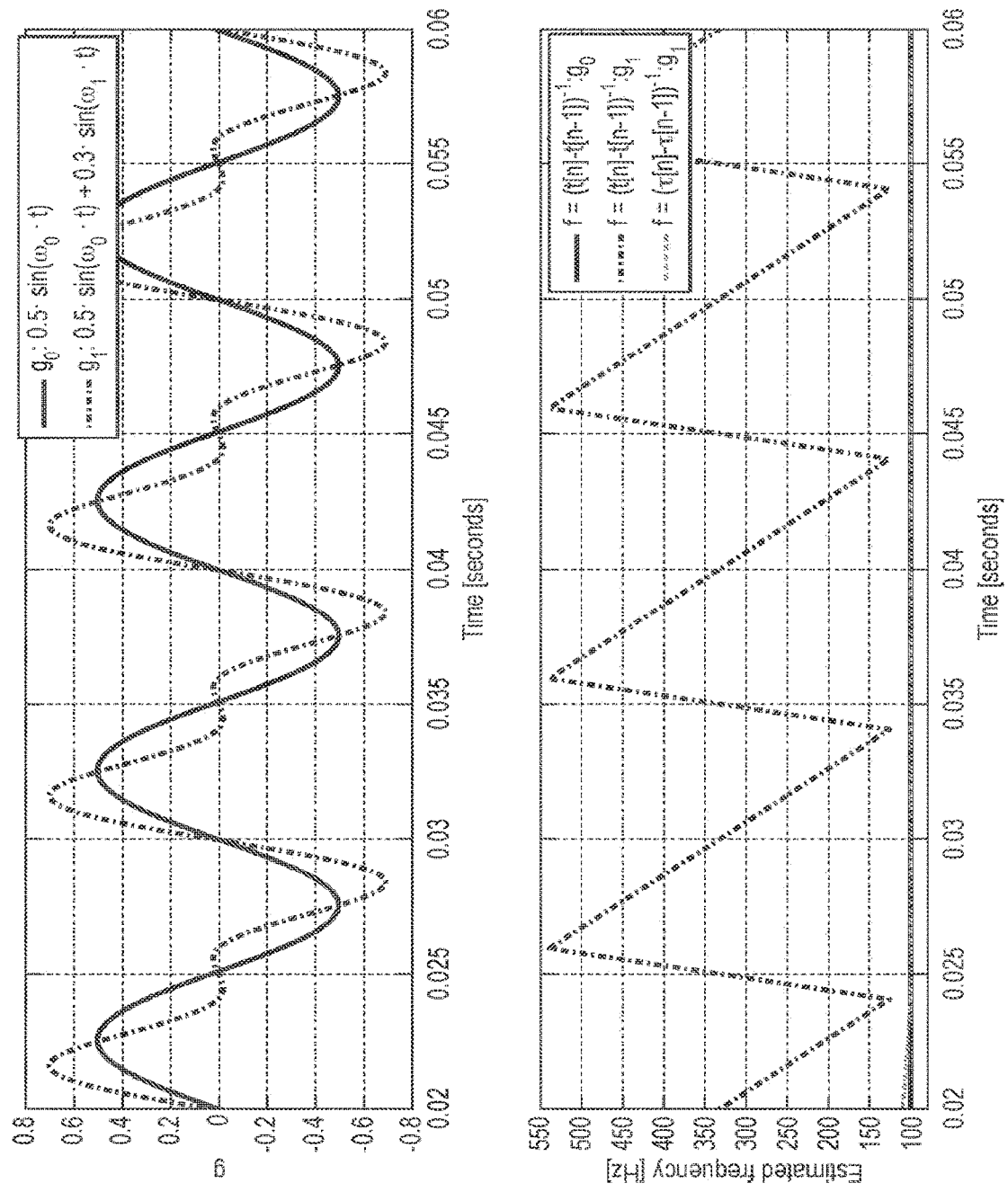
FIG. 8 shows example waveforms for estimation of instantaneous frequency of simple signals.

FIG. 8 shows example waveforms for estimation of instantaneous frequency of simple signals that illustrate the influence of the Limitation Module 702. The top plot in FIG. 8 shows the functions $g_0(t)=0.5\cdot\sin(\omega_0 t)$ and $g_1(t)=g_0(t)+0.3\cdot\sin(\omega_1 t)$ with $\omega_0=2\pi\cdot 100$ Hz and $\omega_1=2\pi\cdot 200$ Hz. In this situation, the objective of the Fine Structure Detector 303 is to estimate the dominant frequency $$f_0 = \frac{\omega_0}{2\pi} = 100 \text{ Hz}.$$

The bottom plot in FIG. 8 shows the estimated frequencies. The solid and dashed-dotted lines correspond to the estimated frequency $f_{zc}$ by the zero-crossings T[n] of the functions $g_0$ and $g_1$ respectively. The estimation is robust for $g_0$ but fails for $g_1$ and gives values over 500 Hz. But estimating the frequency $f_\tau$ by the band-specific upper frequency limit $f_{up}$ in the Limitation Module 702 yields robust results as shown by the dashed grey line in the bottom plot of FIG. 8.

Smoothing Module 703 is used to further smooth the estimated frequency using a timing smoothing window that is defined by updated fine structure feature history to exclude temporal fine structure features that occur outside the window. The window length can be denoted by an integer M. The Smoothing Module 703 can then initialize the average time difference between M successive zero-crossings by:

$$d[M] = \frac{\tau[M] - \tau[1]}{M-1} = \frac{1}{M-1}\sum_{m=1}^{M-1}(\tau[m+1] - \tau[m]).$$

In one preferred embodiment M may be set to $2^{(n+1)}$ and n any positive natural number, preferably 2, allowing for efficient bit-shift operations instead of binary divisions. The Smoothing Module 703 then updates this time difference by:

$$d[m] = (1-\beta)\cdot d[m-1] + \beta\cdot\frac{\tau[m] - \tau[m-M+1]}{M-1}$$

for each new input signal $\tau[m]$ with a smoothing parameter $0<\beta<1$. The output of the Smoothing Module 703 then is:

$$X[p] = \begin{cases} \tau[m] & \text{for } 1 \leq m, p \leq M \\ X[p-1] + d[m] & \text{for } m, p > M \end{cases}.$$

If is readily understood, that other initializations during $1 \leq m \leq M$ may be used without departing from the spirit of the invention. This provides an estimation of the instantaneous frequency $$f_X[p] = \frac{1}{X[p] - X[p-1]}$$

for m>M. The Smoothing Module 703 can adjust the window length M according to defined needs—e.g., depending on the audio signal type, noise level, or similar user preferences. For example, in case of a poor signal to noise ratio (SNR), a long window may be preferred, while shorter windows may be chosen for higher SNRs. Moreover, β can be adjusted taking into account the same signal-specific or user-dependent considerations. Both parameters M and β may be changed dynamically during operation or set initially during for example fitting the system to user needs.

Figure 1:
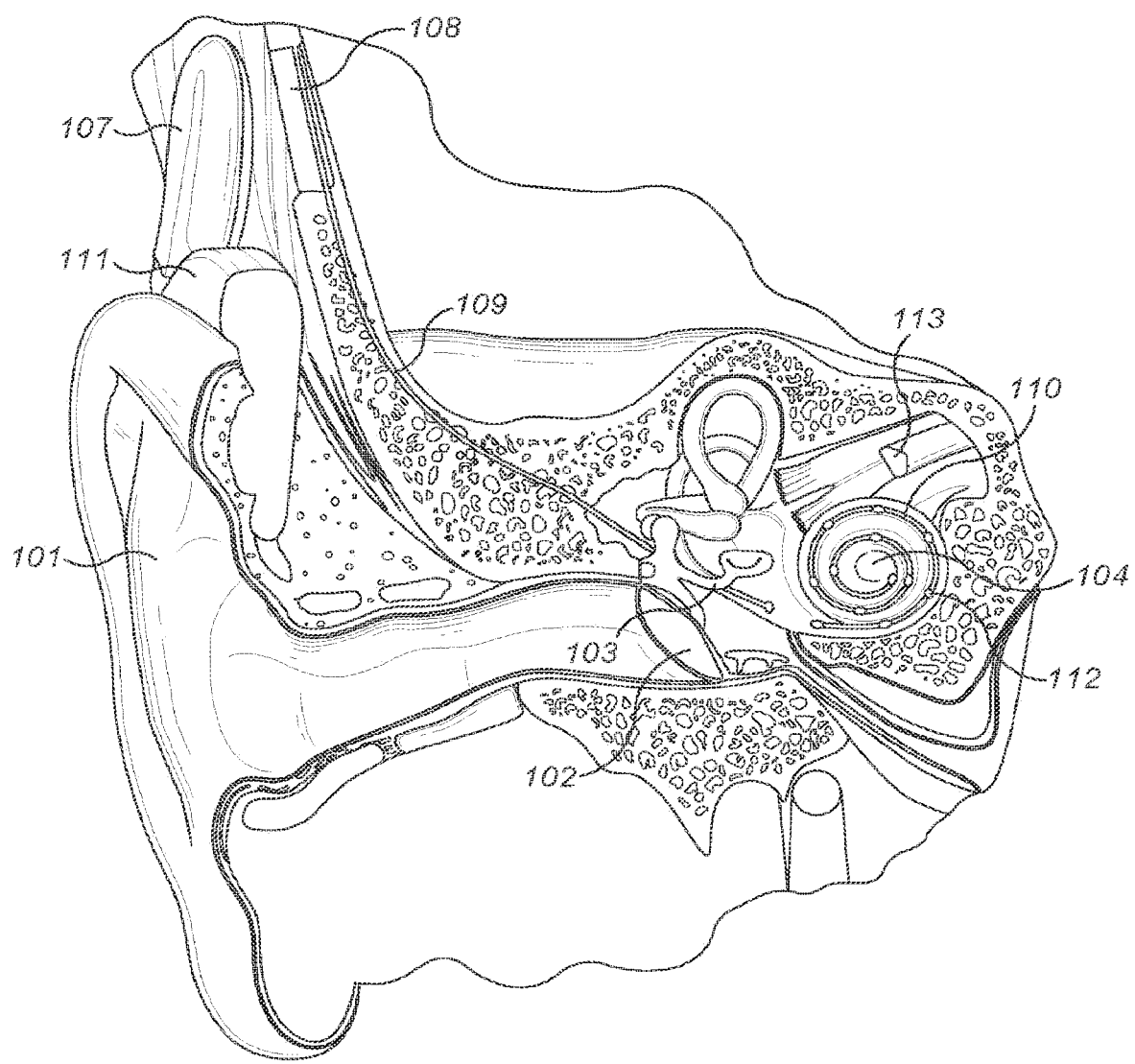
FIG. 1 shows a section view of a human ear with a typical cochlear implant system designed to deliver electrical stimulation to the inner ear.
Figure 2:
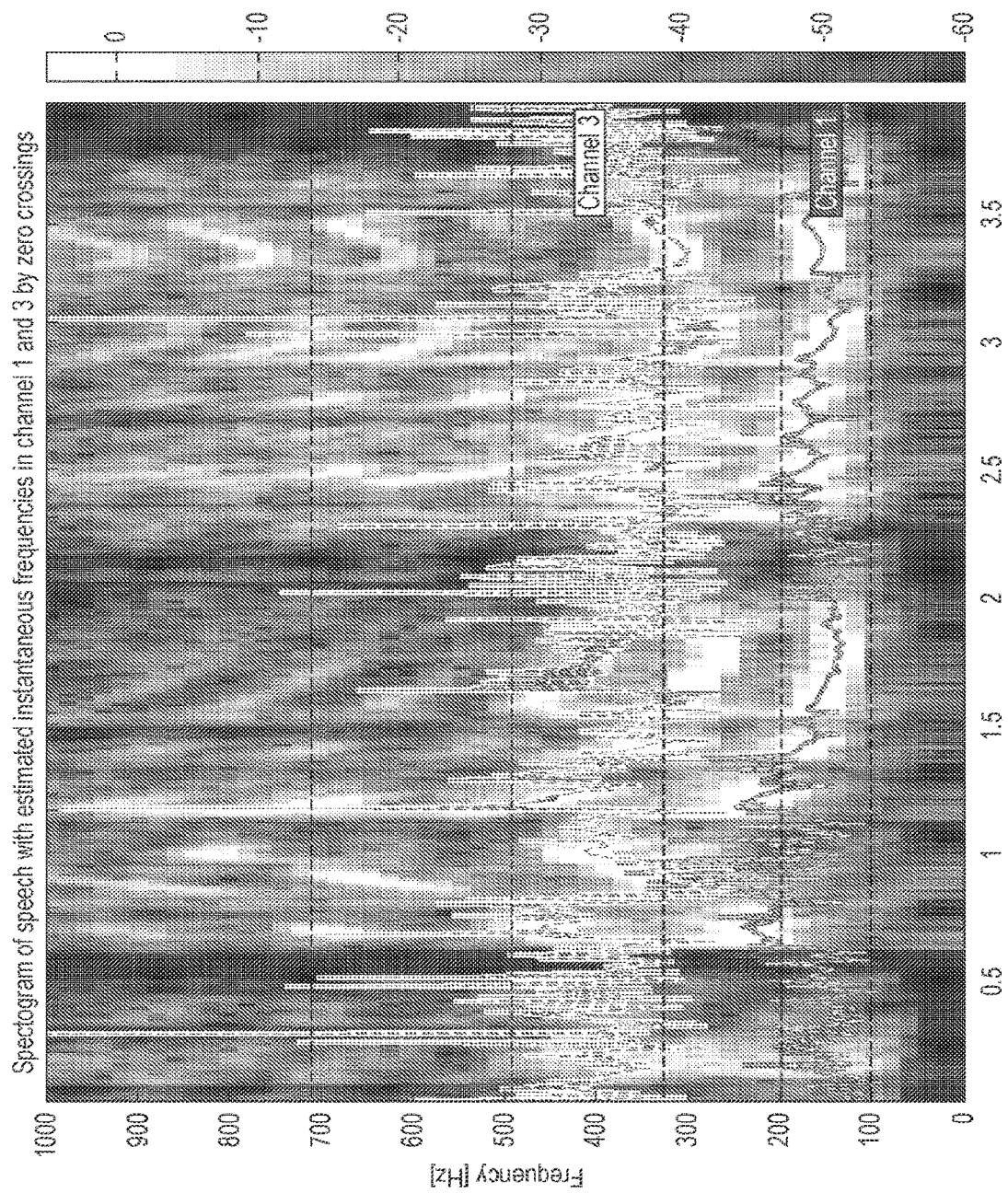
FIG. 2 shows a sample spectrogram for a sample of clean speech including estimated instantaneous frequencies for Channels 1 and 3.
Figure 9:
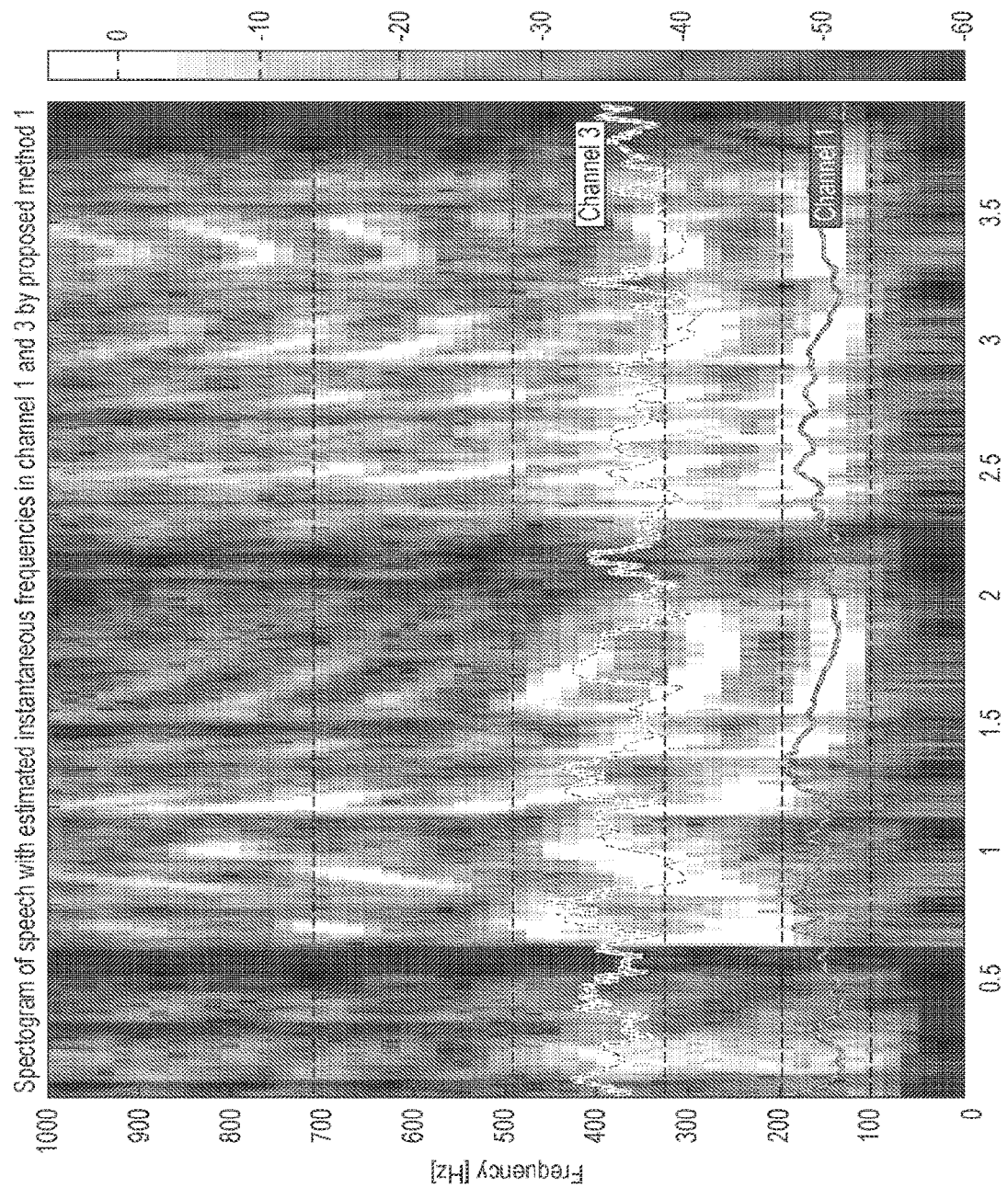
FIG. 9 shows a spectrogram of a clean speech signal with estimated instantaneous frequencies of Channels 1 and 3 according to an embodiment of the present invention.
Figure 10:
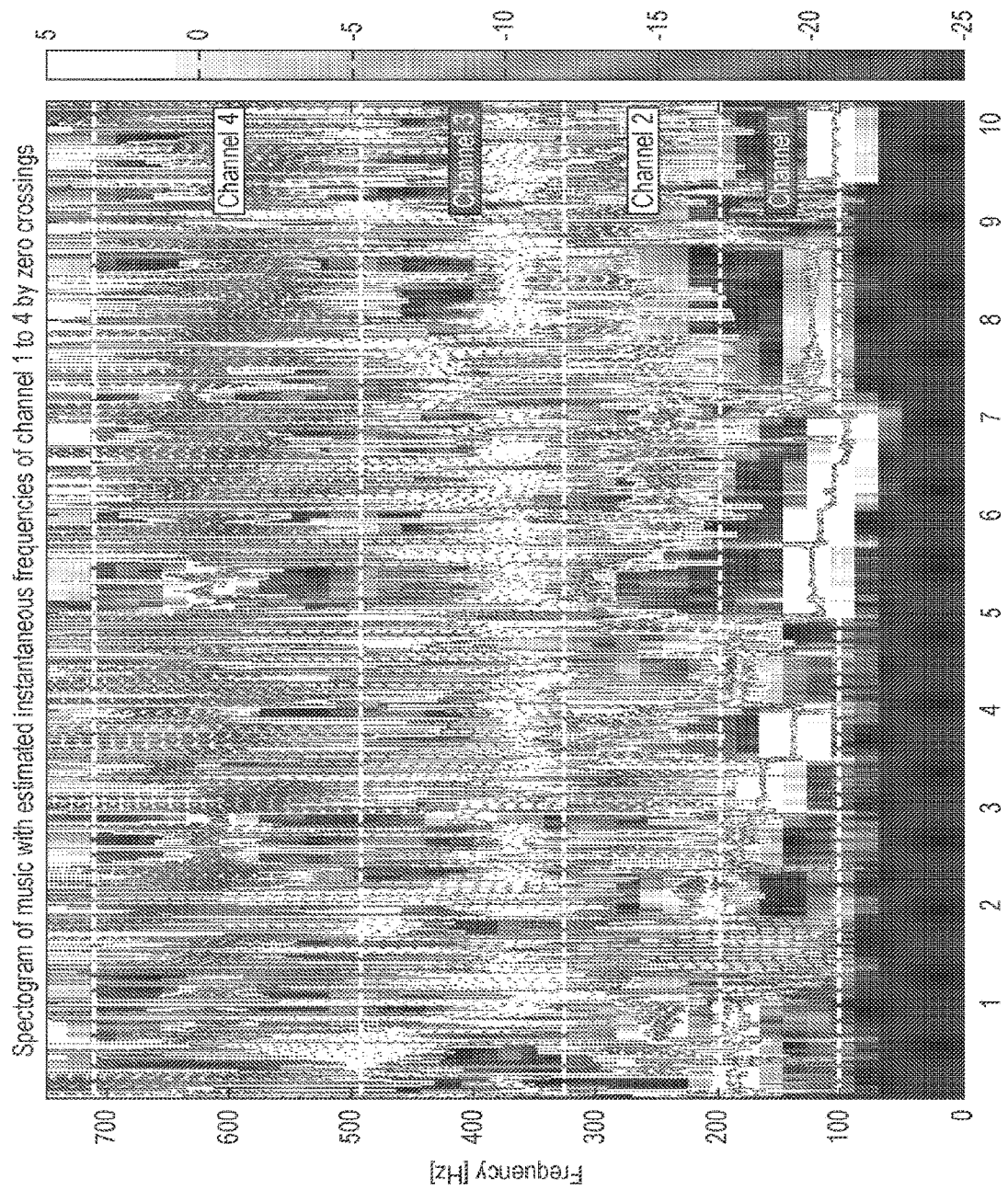
FIG. 10 shows a spectrogram of a music signal with estimated instantaneous frequencies based on zero crossings.
Figure 11:
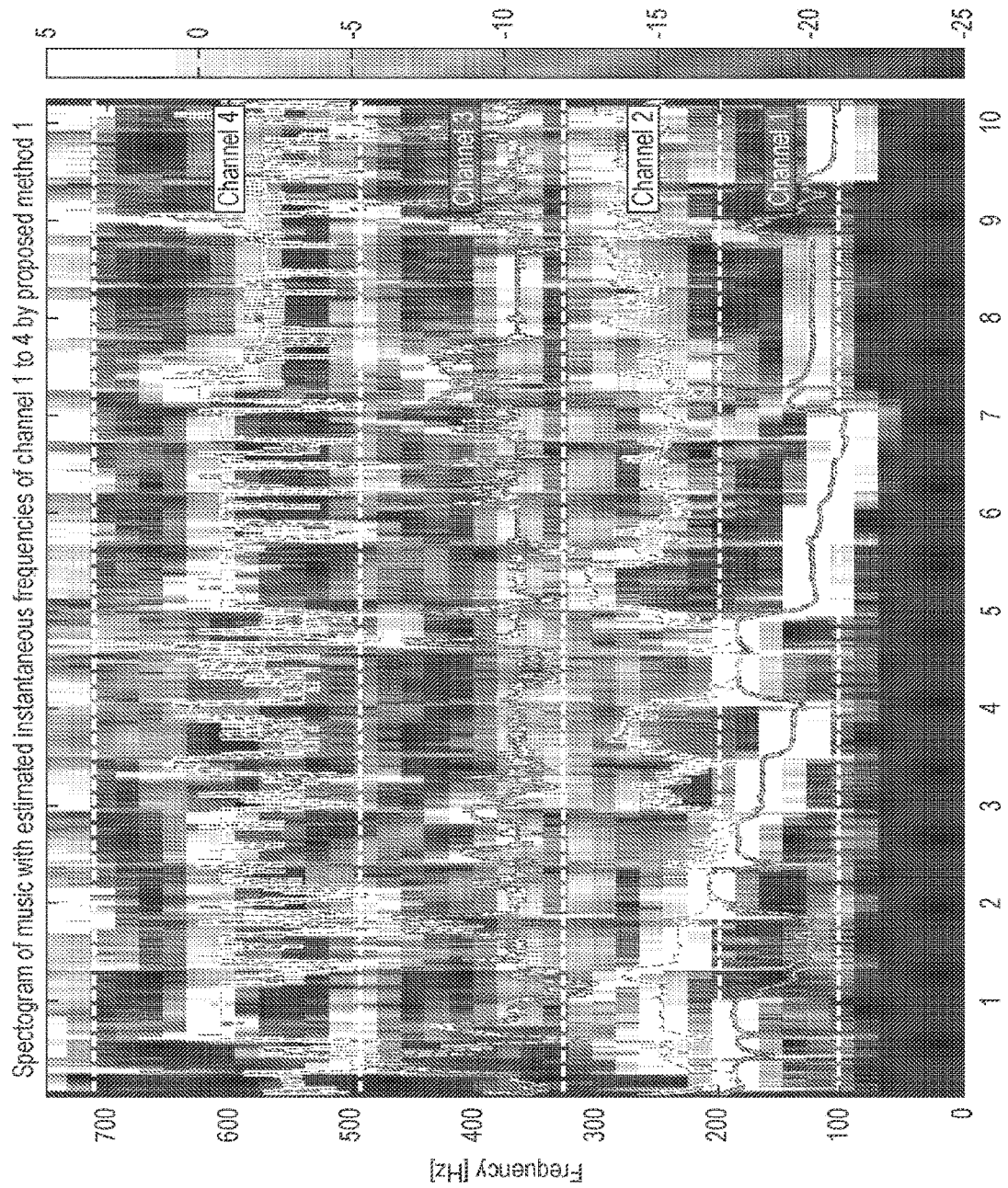
FIG. 11 shows a spectrogram of a music signal with estimated instantaneous frequencies according to an embodiment of the present invention.

FIG. 9 shows the same spectrogram of a speech signal as in FIG. 2, and the estimation of the instantaneous frequency $f_X$ by the Fine Structure Detector 303 of Channels 1 and 3 are also shown. These estimations are smooth and robustly follow the dominant frequency. FIGS. 10 and 11 show a spectrogram for a music sound signal displaying the estimated instantaneous frequencies $f_{zc}$ and $f_x$ of Channels 1 to 4, with the filter bank boundary frequencies being indicated by the white dashed lines. It is clear that in FIG. 10, the basic zero-crossing estimation $f_{zc}$ fails significantly in Channels 2, 3 and 4, and during low intensities, even in Channel 1. By contrast, in FIG. 11, the improved limited and smoothed estimated instantaneous frequency $f_X$ is robust. In some embodiments, a connection over the frequency channels in the Fine Structure Detector 303 can be used to restrict the detection on the fundamental frequency and the corresponding harmonics.

The extracted band-pass signal envelopes $Y_1, \ldots, Y_K$ from the Envelope Detector 302, and the stimulation timing signals $X_1, \ldots, X_K$ from the Fine Structure Detector 303 are input signals to a Pulse Generator 304 that produces the electrode stimulation signals Z for the electrode contacts in the implanted electrode array 305, step 404. The Pulse Generator 304 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 304 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

Figure 16:
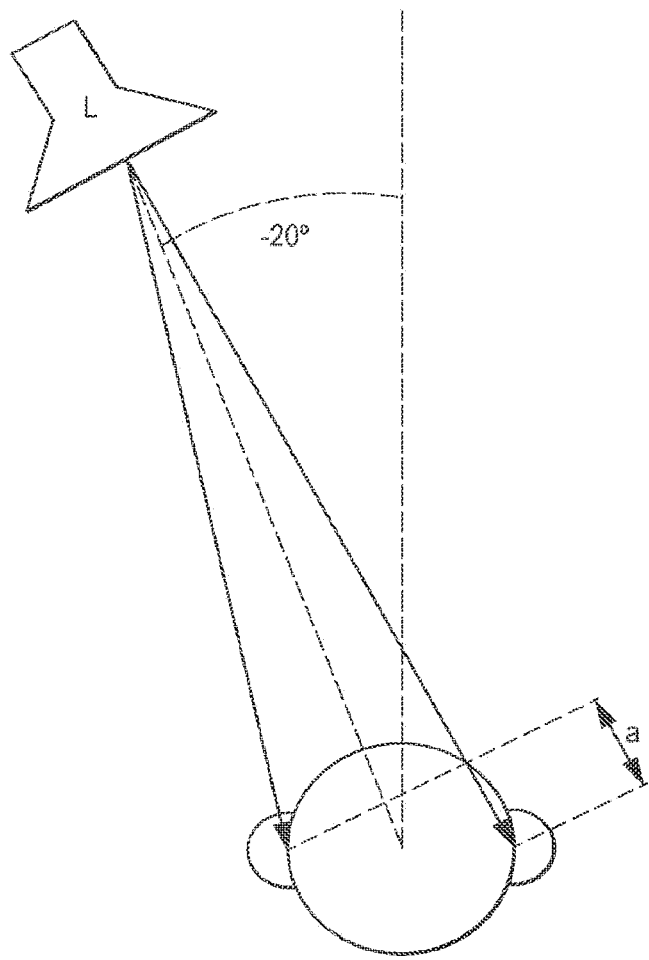
FIG. 16 illustrates the audio principle of interaural time delays (ITDs).

For bilateral system users with implants on each side, fine structure coding strategies such as FSP and FS4 make it possible to transmit the interaural time difference (ITD) of the signal fine structure in low frequency channels. FIG. 16 illustrates the audio principle of interaural time delays (ITDs). The loudspeaker emits a sound signal at −20° in front of a person as shown. This sound propagates with a frequency-dependent velocity $v_s(f)$ and arrives earlier at the left ear than at the right ear because the distance from the sound source to the left ear is shorter than to the right ear. The frequency-dependent ITD is given by the formula $$\Delta t(f) = \frac{a}{v_s(f)},$$

where a is the wave propagation path length difference between left and right ear. This fine structure ITD improves the lateral localization as shown in Majdak et al., "Effects of interaural time differences in fine structure and envelope on lateral discrimination in electric hearing," *Journal of the Acoustical Society of America* 120.4 (2006): 2190-2201; which is incorporated herein by reference in its entirety.

Figure 17:
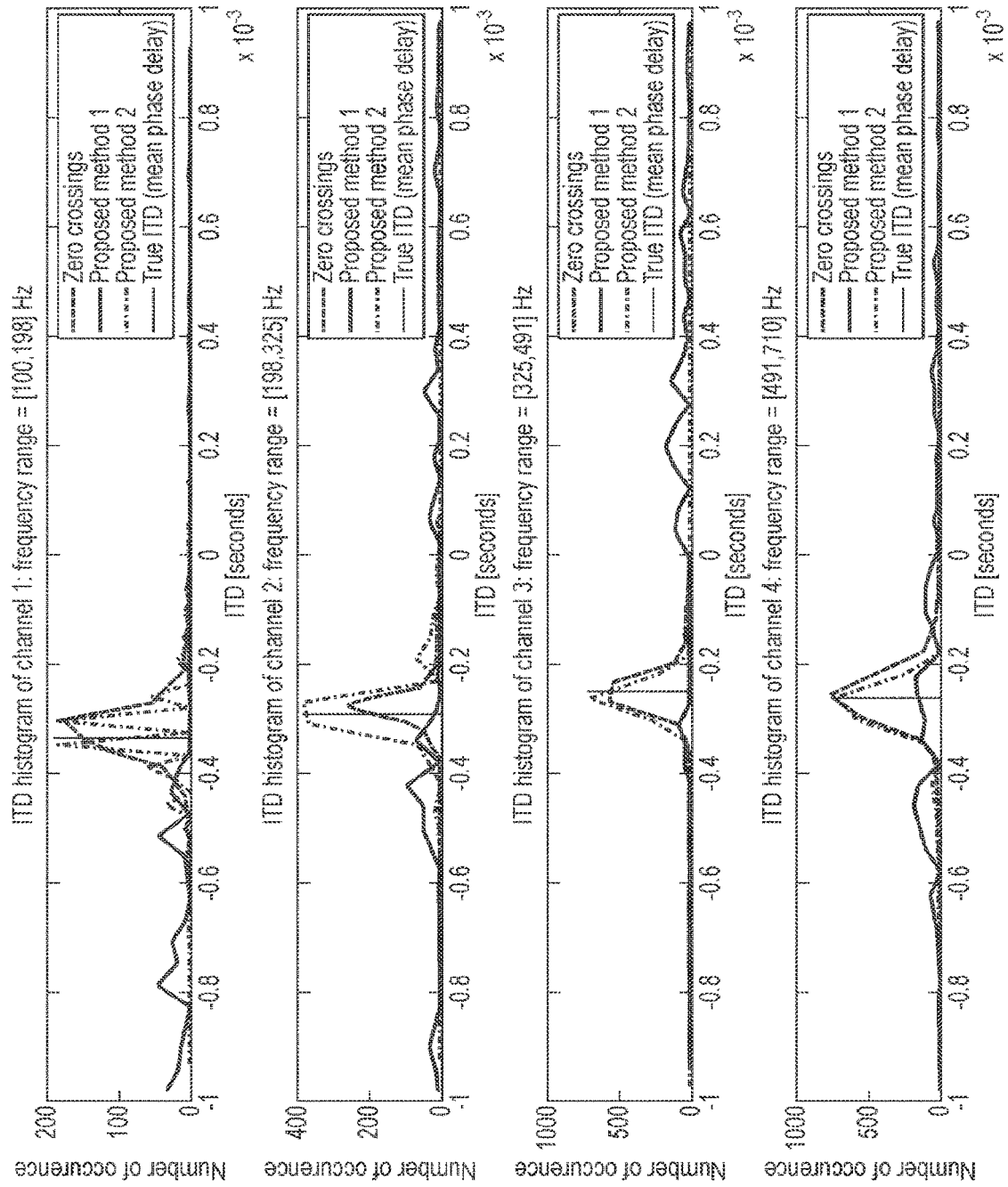
FIG. 17 shows a histogram plot of estimated ITDs of Channels 1-4.

One disadvantage of the process for detection of fine structure information discussed above is that the fine structure ITDs will not be transmitted. In FIG. 17, the ITD Δt of the four lowest frequency Channels 1-4 is shown by the solid black vertical lines at −33, −29, −25 and −26 milliseconds, respectively. The zero-crossings of the band pass signals $U_k$ appear with the same delay Δt(f) between the left and the right ear. Thus, the fine structure ITD information is transmitted using the timing T[n]. This is shown by the black dashed lines.

Smoothing Module 703 as specifically discussed above will blur the ITD information (see grey solid line). Thus, in some embodiments, the Smoothing Module 703 may be modified to operate differently so as to improve this ITD information. This modified step may be followed by the mode step as described before to preserve the ITD information during the onset period. The averaged time difference d is calculated as above, but the generation of the output is modified using:

$$X[p] = \begin{cases} \tau[m] & \text{if} \quad 1 \leq m, p \leq M \\ \tau[m] & \text{if} \quad \tau[m] - X[p-1] > \frac{1}{f_{up}} \text{ and } m, p > M \\ X[p-1] + d[m-1] + \delta_f & \text{if} \quad \tau[m] - X[p-1] > d[m-1] + \delta_t \text{ and } m, p > M \end{cases},$$

where $\delta_t$ is a channel-specific parameter. This approach yields for the output X and the resulting estimated frequency $f_x$:

- Limitation Module 702 will ignore zero-crossings T[n] that are too fast, and so $f_x \leq f_{up}$.
- Zero-crossings that are too slow, (τ[m]>X[p−1]+d[m−1]+ $\delta_t$), only influence the estimation of the averaged time difference d and not the output X. This results in a smoothed estimated frequency:

$$f_X[p] \geq \frac{1}{d[m-1] + \delta_t}.$$

In this case, the fine structure ITDs are not actualized.

In the remaining case, the zero-crossings occur in the interval:

$$X[p-1] + \frac{1}{f_{up}} < \tau[m] \leq X[p-1] + d[m-1] + \delta_t.$$

In that case, the output X[p]=τ[m] and the actual ITDs are transmitted.

Note that by decreasing the parameter $\delta_f$, the fine structure ITD transmission degrades while simultaneously the frequency estimation results in a smoother estimate evolution.

Figure 18:
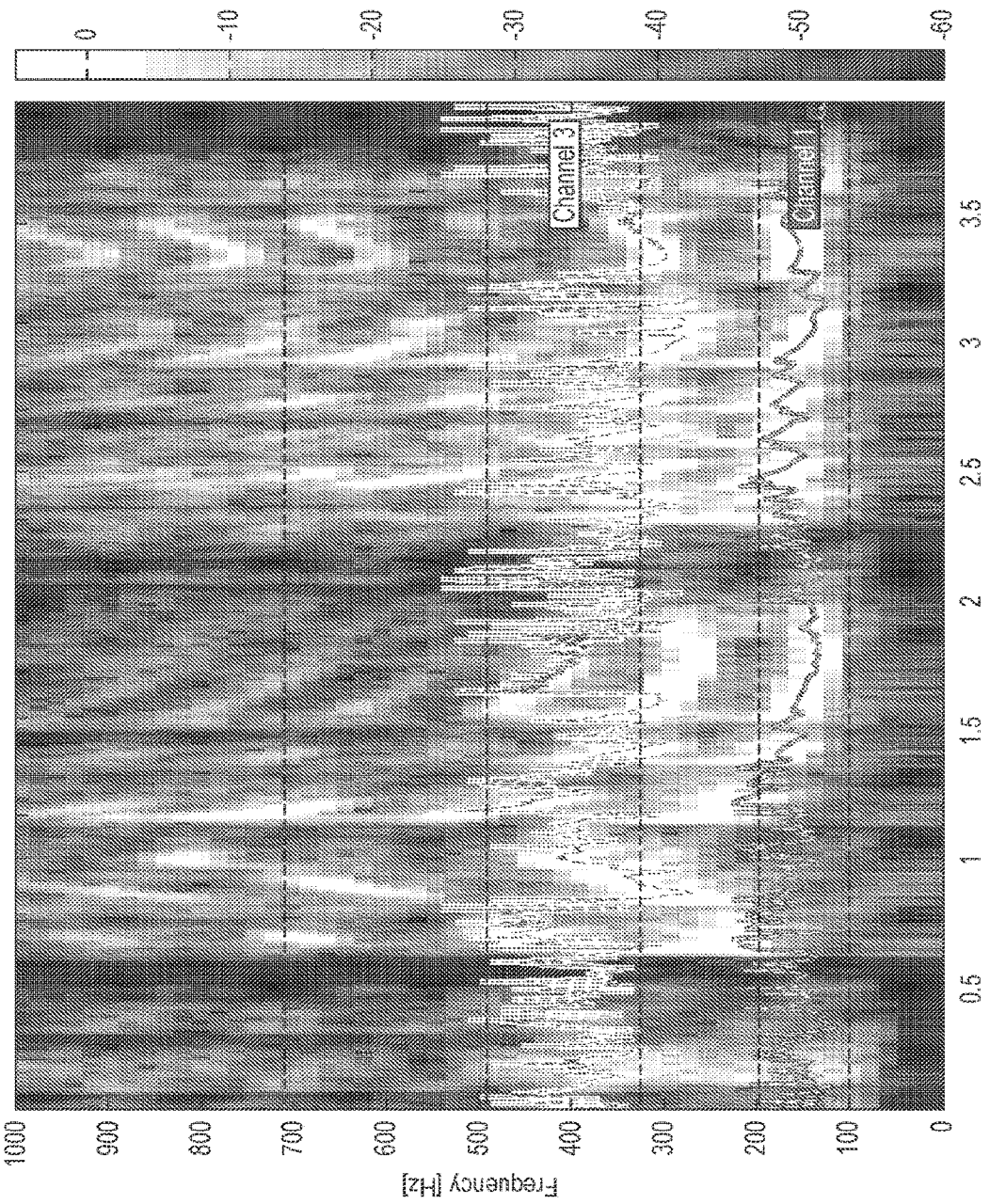
FIG. 18 shows a spectrogram of a clean speech signal with estimated instantaneous frequencies of Channels 1 and 3 according to another embodiment of the present invention.

The resulting ITD transmission is shown by the grey dashed lines in FIG. 17. These are comparable to the results of the zero-crossing transmission. In FIG. 18, the spectrogram of the same signal as before is shown, along with the instantaneous frequency estimates of Channels 1 and 3 produced as per the modified process just described. The estimation is clearly more accurate and smoother than $f_{zc}$ but not as accurate and smooth as with the original smoothing process.

In some embodiments, the Smoothing Module 703 may also include a voice-activity detector (VAD). The zero-crossings are not reliable during periods with low signal intensities, which adversely affects the estimation of the instantaneous frequency during that time. Thus, an update of d may be done only when the VAD detects that speech is active (i.e., high signal intensity), and setting d[m]=d[m−1] when there is no speech detected (i.e., low signal intensity). During such speech, the output signal is generated by X[m]=X[m−1]+d[m], which leads to a constant instantaneous frequency during speech pauses. Other smoothing methods to generated and/or X can be chosen.

In some further embodiments, the Smoothing Module 703 may be modified to operate in an alternative way to improve ITD information or in addition to further improve ITD information as described above. This is described in more detail below. Returning to a simplified discussion with only one band pass channel and neglecting the channel index, then T[n] denotes the point in time when the $n^{th}$ zero-crossing is detected, and τ[m] is the point in time where the $m^{th}$ limited zero-crossing is detected. Then the estimated frequencies are:

$$f_{zc}[n] = \frac{1}{\tau[n] - \tau[n-1]} \text{ and } f_{lim}[m] = \frac{1}{\tau[m] - \tau[m-1]}.$$

Figure 12:
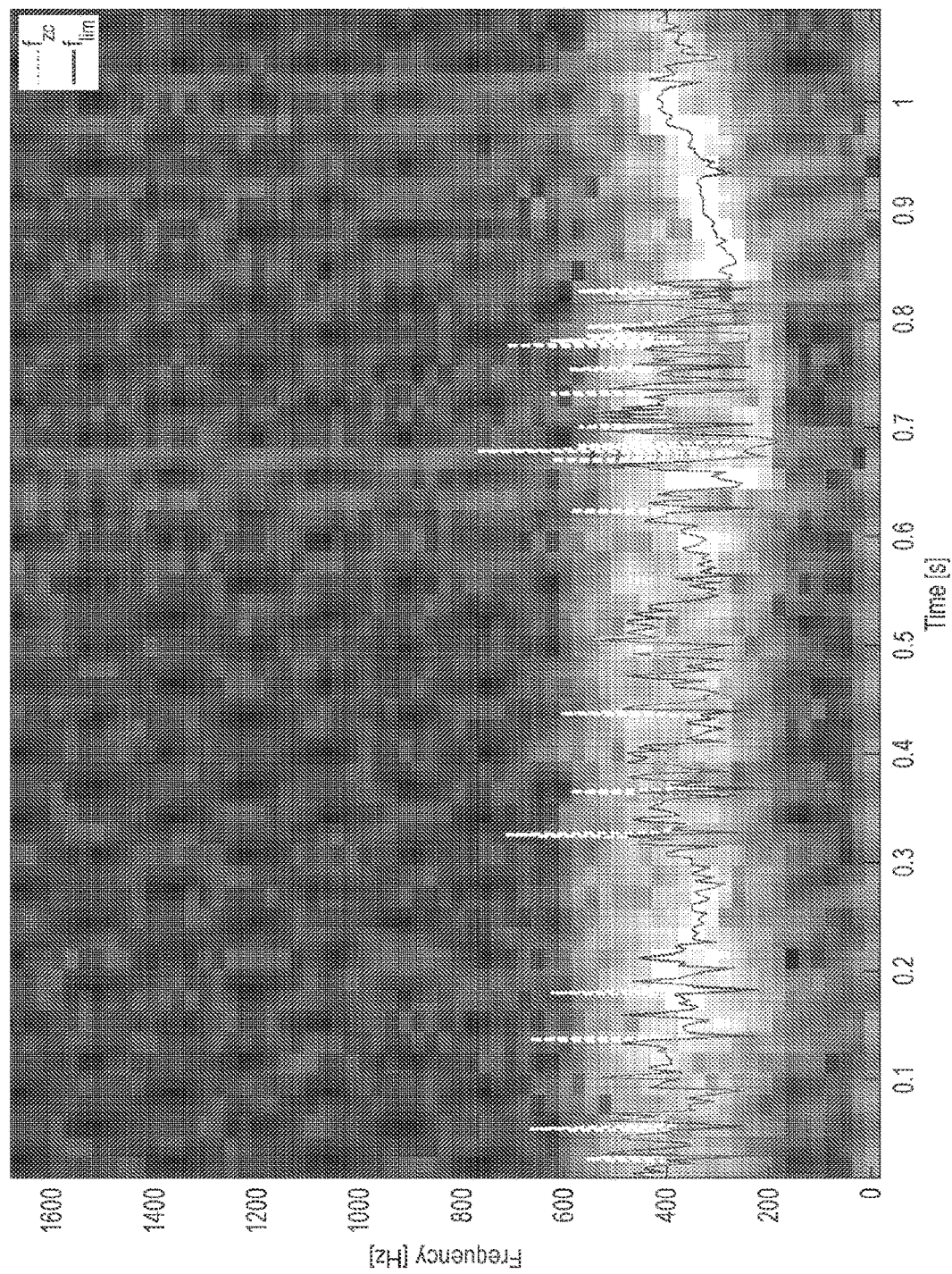
FIG. 12 shows an example spectrogram of channel 3 band pass signal with estimated frequencies of the zero-crossings and limited estimated zero-crossings.

FIG. 12 shows a spectrogram of the channel 3 band-pass signal and the estimated frequencies with the light dashed lines showing the estimated frequencies of the zero-crossing $f_{zc}$ and the solid dark line showing the limited zero-crossings $f_{lim}$. In this example, the estimation of the zero-crossing estimated frequency $f_{zc}$ is robust when a strong dominant frequency is present in the channel (e.g., in the interval from 0.85 to 1.0 seconds), but during for example unresolved harmonics (e.g., from 0.65-0.82 seconds), the estimated frequency $f_{zc}$ leaves the transition range of the band-pass filter. This also occurs when the channel energy is low. This can be avoided by restricting the time interval between two successive zero-crossings as discussed above by discarding the timing information of the zero-crossings and concentrating on a smooth estimation of the instantaneous frequency. In one embodiment, the same smooth frequency estimation can be performed, but during the onset of the band-pass envelope signal, the timing information of the limited zero-crossing may be preserved.

Figure 13:
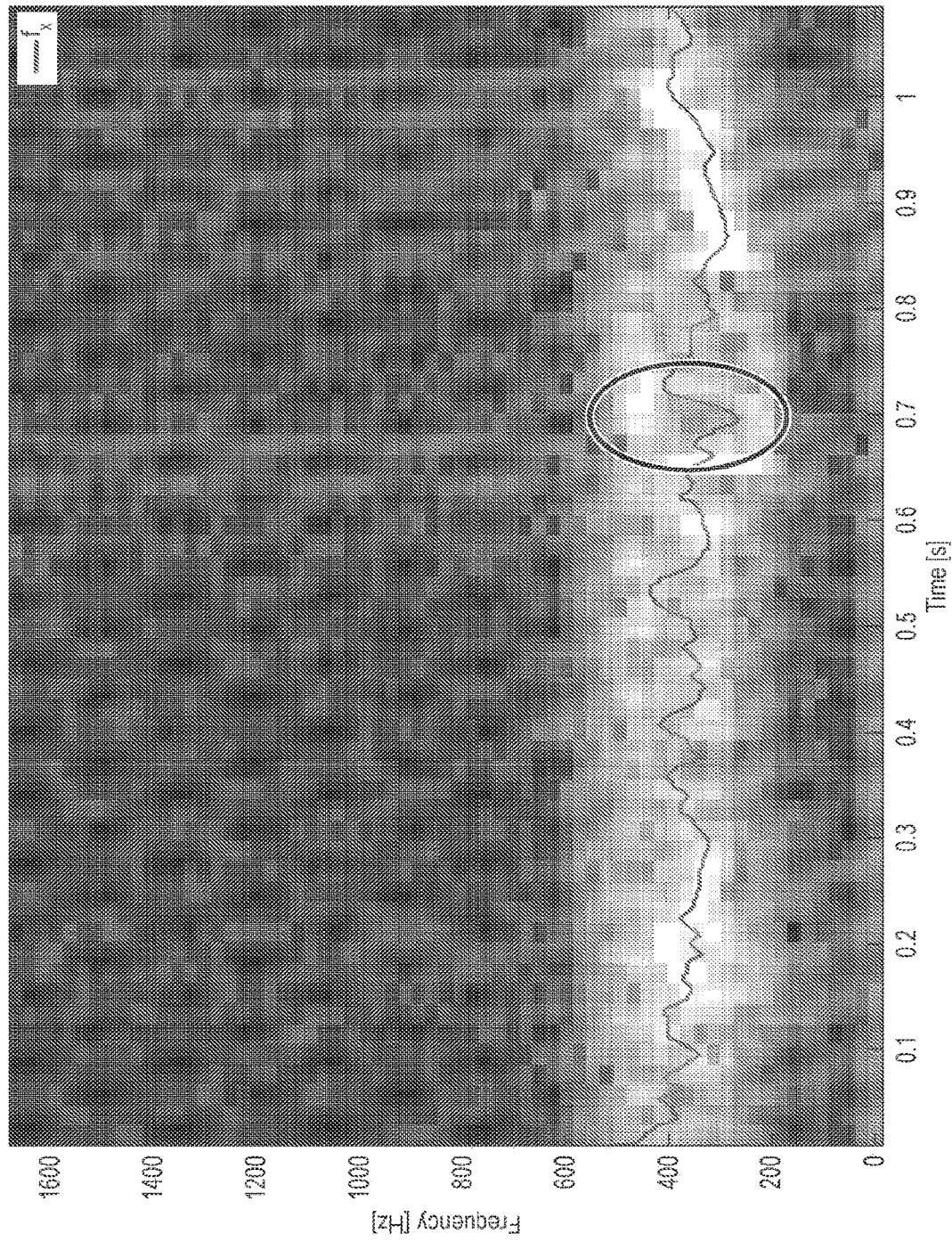
FIG. 13 shows the example spectrogram of FIG. 12 with uniform smoothing applied.

FIG. 13 shows the resulting estimated frequency $f_x$ for the example spectrogram shown in FIG. 12 using the algorithm previously described above. The estimated frequency is smoothed and the dominant instantaneous frequency is well-estimated. When for example unresolved harmonics are present, there is a tendency to the dominant frequency (the thick ellipse highlight in FIG. 13), but the delay caused by the smoothing is also visible. The timing information of the smoothed zero-crossings is blurred by the smoothing, which may hamper the otherwise helpful timing information for localization or speech intelligibility. To gain both advantages, the smoothed zero-crossings can be transmitted in general, but the timing of the limited zero-crossings is kept for $T_{onset}$ seconds after an onset of the band-pass envelope signal is detected. Following the $T_{onset}$ seconds period, for another $T_{inhib}$ seconds any further detected onset of the band-pass envelope signal is ignored.

More specifically, use Y[l] and dY[l]=Y[l]−Y[l−1] to refer to the envelope value and the slope of the envelope value, respectively, with time index l. Then the onset of the band pass envelope signal is defined to occur if Y[l]>$thr_{env}$ and/or dY[l]>$thr_{denv}$ is fulfilled. And use $\tilde{X}$[q] in the following to denote the point in time when the $q^{th}$ modified zero-crossing is transmitted to the output of Smoothing Module 703. Then three modes can be defined—"general", "onset" and "inhibition"—for controlling the selection of the output $\tilde{X}$. During the onset mode, the limited zero-crossing timings are used: $\tilde{X}$[q]=τ[m]. During the inhibition mode and the general mode, the smoothed zero-crossings are transmitted: $\tilde{X}$[q]=X [l]. The difference between these two time modes is that during the inhibition mode, further detected onsets are ignored.

If t is the current time, then pseudo code for such an arrangement can be set forth as follows:

```
If mode == "general"
    Transmit smoothed zero-crossing: X̃[q] = X[p].
    If an onset is detected
                        mode = "onset"
                        t_startOnset = t
Elseif mode == "onset"
    Transmit limited zero-crossing: X̃[q] = τ[m]
    If t − t_startOnset == T_onset
                        mode = "inhibition"
                        t_startInhib = t
Elseif mode == "inhibition"
    Transmit smoothed zero-crossing: X̃[q] = X[p].
    If t − t_startInhib == T_inhib
                        mode = "general"
```

Figure 14:
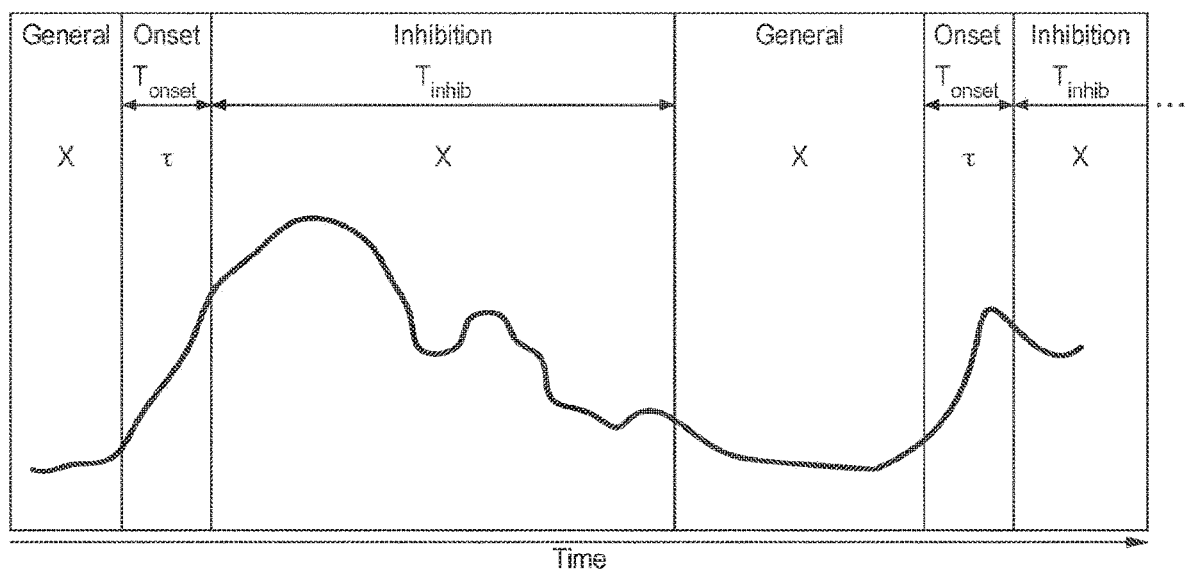
FIG. 14 shows an example of using three different time modes according to an embodiment of the present invention.
Figure 15:
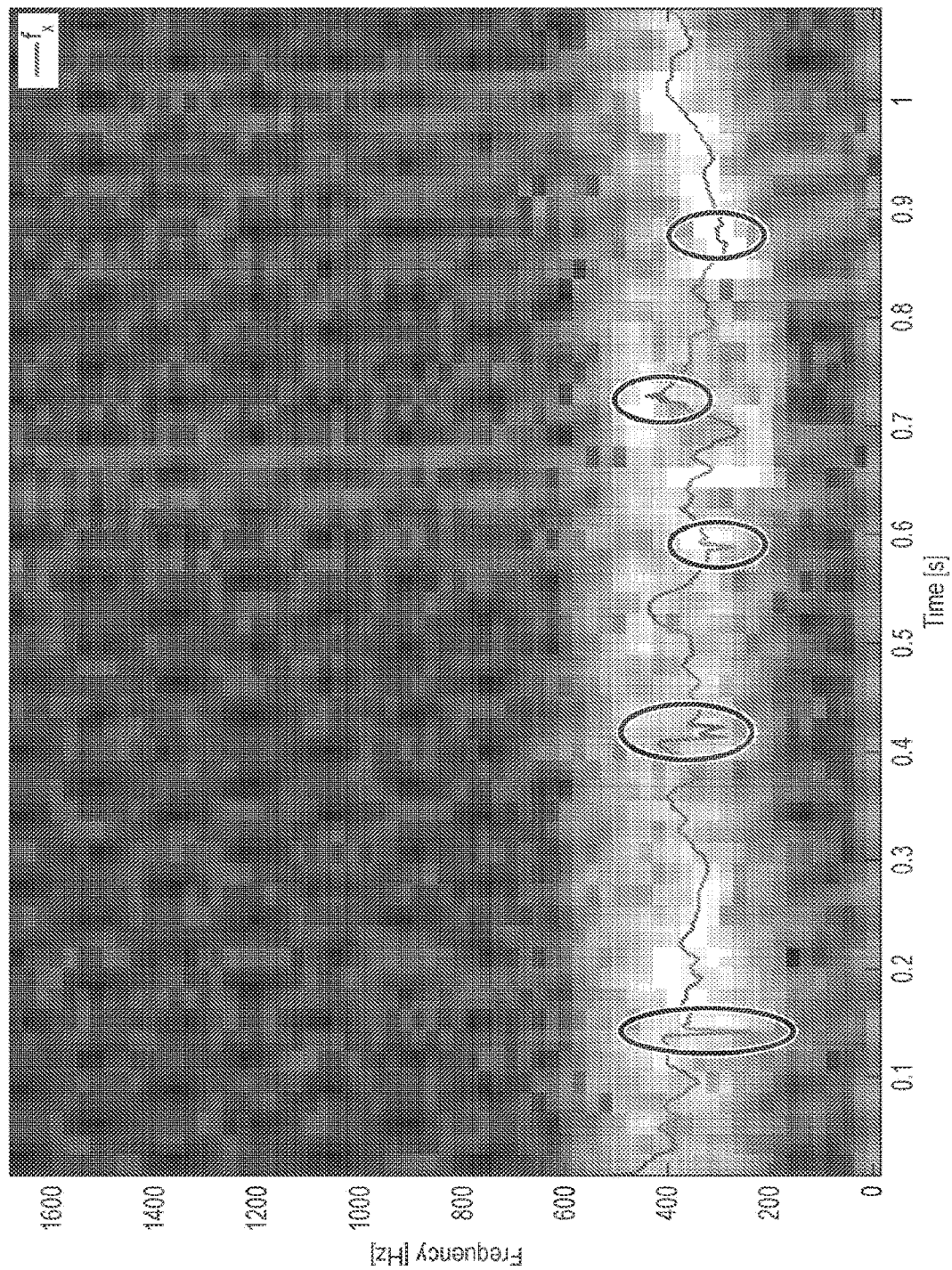
FIG. 15 shows a spectrogram of channel 3 with three time modes where the thick ellipses indicate the regions of the onset stimulation.

FIG. 14 shows a graphic depiction of one example of such an approach where the thick black curve shows the band pass envelope for the channel. Initially, the general mode is active as indicated by the light background. During that time, the smoothed zero-crossings X are transmitted to the output. Then the band pass envelope rises, which is detected as an onset, and which changes the mode to onset mode as indicated by the medium gray background. During the onset mode, the limited zero-crossing timings are transmitted to the output. After $T_{onset}$ seconds, the mode changes to inhibition mode, which lasts for $T_{inhib}$ seconds. After that, the general mode becomes active again. During these two periods the smoothed zero-crossings X are transmitted to the output. At the time when the next onset is detected, the same process restarts. FIG. 15 shows a spectrogram of channel 3 with the revised process where the thick ellipses indicate the regions of the onset stimulation. This shows that overall, a robust estimation of the dominant frequency is achieved, and during envelope onsets, the timing information of the zero-crossings is kept.

In some embodiments, the smoothed zero-crossings X can be dynamically adapted. And other features besides band pass envelope signal onset detection can be used to control the modes; for example, increasing SNR or known voice-activity detector based methods. All these methods may be used in a channel specific manner, i.e. onset determination of a per channel basis or over all channels simultaneously. In some bilateral systems, the left and right systems can be coupled for bilateral probands; for example, coherent coupling of the onset detection.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for generating electrode stimulation signals for electrode contacts in an implanted cochlear implant electrode array, the method comprising:
   processing an input sound signal to generate a plurality of band pass signals, each band pass signal representing an associated band of audio frequencies, and each band pass signal having amplitude and temporal fine structure features;
   extracting a characteristic envelope signal for each band pass signal based on its amplitude;
   generating stimulation timing signals for each band pass signal, wherein for one or more selected band pass signals the stimulation timing signals are generated based on a timing function defined to:
      i. represent instantaneous frequency as determined by the band pass signal temporal fine structure features,
      ii. exclude temporal fine structure features occurring within a time period shorter than a band-specific upper frequency limit, and
      iii. exclude temporal fine structure features occurring outside a timing smoothing window defined by updated fine structure feature history; and
   producing the electrode stimulation signals for each electrode contact based on the envelope signals and the stimulation timing signals.

2. The method according to claim 1, wherein the band pass signal temporal fine structure features used by the timing function include zero crossings of the band pass signal.

3. The method according to claim 1, wherein stimulation timing signals for the one or more selected band pass signals are Channel-Specific Sampling Sequences (CSSS).

4. A method for generating electrode stimulation signals for electrode contacts in an implanted cochlear implant electrode array, the method comprising:
   processing an input sound signal to generate a plurality of band pass signals, each band pass signal representing an associated band of audio frequencies, and each band pass signal having amplitude and temporal fine structure features;
   extracting a characteristic envelope signal for each band pass signal based on its amplitude;
   generating stimulation timing signals for each band pass signal, wherein for one or more selected band pass signals the stimulation timing signals are generated based on a timing function defined to:
      i. represent instantaneous frequency as determined by the band pass signal temporal fine structure features,
      ii. exclude temporal fine structure features occurring within a time period shorter than a band-specific upper frequency limit, and
      iii. preserve fine structure interaural time difference (ITD) information present in the input sound signal; and
   producing the electrode stimulation signals for each electrode contact based on the envelope signals and the stimulation timing signals.

5. The method according to claim 1, wherein the timing function further is defined without regard to preserving fine structure interaural time difference (ITD) information present in the input sound signal.

6. The method according to claim 1, wherein extracting the characteristic envelope signals includes using low pass filters.

7. The method according to claim 1, wherein extracting the characteristic envelope signals includes using Hilbert filters.

8. The method according to claim 1, wherein stimulation timing signals for a plurality band pass signals are generated without the timing function, using Continuous Interleaved Sampling (CIS) coding.

9. The method according to claim 1, wherein the timing function is further defined to identify an onset period of the band pass envelope signal and not apply the timing smoothing window during the onset period.

10. The method according to claim 1, wherein the timing smoothing window is defined using a voice activity detector (VAD).

11. A system for generating electrode stimulation signals to electrode contacts in an implanted cochlear implant electrode array, the arrangement comprising:
- a preprocessor filter bank configured to process an input sound signal to generate a plurality of band pass signals, each band pass signal representing an associated band of audio frequencies, and each band pass signal having amplitude and temporal fine structure features;
- an envelope detector configured to extract a characteristic envelope signal for each band pass signal based on its amplitude;
- a fine structure detector configured to generate stimulation timing signals for each band pass signal, wherein for one or more selected band pass signals, the fine structure detector generates the stimulation timing signals based on a timing function defined to:
  - i. represent instantaneous frequency as determined by the band pass signal temporal fine structure features,
  - ii. exclude temporal fine structure features occurring within a time period shorter than a band-specific upper frequency limit, and
  - iii. exclude temporal fine features occurring outside a timing smoothing window defined by updated fine structure feature history; and
- a pulse generator configured to produce the electrode stimulation signals for each electrode contact based on the envelope signals and the stimulation timing signals.

12. The system according to claim 11, wherein fine structure detector uses a timing function in which the band pass signal temporal fine structure features include zero crossings of the band pass signal.

13. The system according to claim 11, wherein the fine structure detector is configured to use Channel-Specific Sampling Sequences (CSSS) to generate the stimulation timing signals.

14. A system for generating electrode stimulation signals to electrode contacts in an implanted cochlear implant electrode array, the arrangement comprising:
- a preprocessor filter bank configured to process an input sound signal to generate a plurality of band pass signals, each band pass signal representing an associated band of audio frequencies, and each band pass signal having amplitude and temporal fine structure features;
- an envelope detector configured to extract a characteristic envelope signal for each band pass signal based on its amplitude;
- a fine structure detector configured to generate stimulation timing signals for each band pass signal, wherein for one or more selected band pass signals, the fine structure detector generates the stimulation timing signals based on a timing function defined to:
  - i. represent instantaneous frequency as determined by the band pass signal temporal fine structure features, and
  - ii. exclude temporal fine structure features occurring within a time period shorter than a band-specific upper frequency limit, and
  - iii. preserve fine structure interaural time difference (ITD) information present in the input sound signal; and
- a pulse generator configured to produce the electrode stimulation signals for each electrode contact based on the envelope signals and the stimulation timing signals.

15. The system according to claim 11, wherein fine structure detector uses a timing function further defined without regard to preserving fine structure interaural time difference (ITD) information present in the input sound signal.

16. The system according to claim 11, wherein the envelope detector is configured to use low pass filters for extracting the characteristic envelope signals.

17. The system according to claim 11, wherein the envelope detector is configured to use Hilbert filters for extracting the characteristic envelope signals.

18. The system according to claim 11, wherein the fine structure detector is further configured to generate stimulation timing signals for a plurality band pass signals without the timing function, using Continuous Interleaved Sampling (CIS) coding.

19. The system according to claim 11, wherein the fine structure detector is configured to identify an onset period of the band pass envelope signal and not apply the timing smoothing window during the onset period.

20. The system according to claim 11, wherein the timing smoothing window is defined using a voice activity detector (VAD).

21. A non-transitory tangible computer-readable medium having instructions thereon for generating electrode stimulation signals to electrode contacts in an implanted cochlear implant electrode array, the instructions comprising:
- processing an input sound signal to generate a plurality of band pass signals, each band pass signal representing an associated band of audio frequencies, and each band pass signal having amplitude and temporal fine structure features;
- extracting a characteristic envelope signal for each band pass signal based on its amplitude;
- generating stimulation timing signals for each band pass signal, wherein for one or more selected band pass signals the stimulation timing signals are generated based on a timing function defined to:
  - i. represent instantaneous frequency as determined by the band pass signal temporal fine structure features,
  - ii. exclude temporal fine structure features occurring within a time period shorter than a band-specific upper frequency limit; and
  - iii. exclude temporal fine structure features occurring outside a timing smoothing window defined by updated fine structure feature history; and
- producing the electrode stimulation signals for each electrode contact based on the envelope signals and the stimulation timing signals.

* * * * *